(12) United States Patent
Wu et al.

(10) Patent No.: US 9,353,079 B2
(45) Date of Patent: May 31, 2016

(54) SOLID FORMS OF AN ALPHA, OMEGA DI-SUBSTITUTED DIHYDROXY CYCLOPENTYL COMPOUND AND METHODS FOR THE PREPARATION AND USE THEREOF

(71) Applicant: Allergan, Inc., Irvine, CA (US)

(72) Inventors: Ke Wu, Irvine, CA (US); Gyorgy F. Ambrus, Santa Ana, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 14/569,210

(22) Filed: Dec. 12, 2014

(65) Prior Publication Data

US 2015/0166504 A1     Jun. 18, 2015

Related U.S. Application Data

(60) Provisional application No. 61/915,575, filed on Dec. 13, 2013.

(51) Int. Cl.
   *C07D 333/28*     (2006.01)

(52) U.S. Cl.
   CPC .................................. *C07D 333/28* (2013.01)

(58) Field of Classification Search
   CPC ...................................................... C07D 333/28
   USPC ........................................................ 514/438
   See application file for complete search history.

(56) References Cited

U.S. PATENT DOCUMENTS 6,124,344 A * 9/2000 Burk .............................. 514/438
6,602,900 B2    8/2003 Burk

FOREIGN PATENT DOCUMENTS

WO       9925358       5/1999

OTHER PUBLICATIONS

Caira, Mino R., Crystalline Polymorphism of Organic Compounds, Topics in Current Chemistry 1998, 198: 164-208.
Notification of Transmittal of the International Search Report and Written Opinion of the International Searching Authority mailed on Feb. 5, 2015 for PCT/US2014/070156 filed on Dec. 12, 2014 in the name of Allergan, Inc.

* cited by examiner

*Primary Examiner* — Taofiq A Solola
(74) *Attorney, Agent, or Firm* — Jonathan Bass

(57) ABSTRACT

Provided herein are multiple solid forms of a defined α,ω-disubstituted dihydroxy cyclopentyl compound, and methods for the preparation and use thereof. In one aspect, there are provided crystalline forms of said cyclopentyl compound, and methods for the preparation and use thereof. In another aspect, there are provided substantially amorphous forms of said dihydroxy cyclopentyl compound, and methods for the preparation and use thereof. In yet another aspect, there are provided compositions containing compounds according to the present invention. In certain aspects, such compositions are suitable for delivery of active agents according to the present invention to a subject in need thereof. In another aspect of the invention, there are provided methods for the treatment of a variety of indications, including glaucoma, ocular hypertension, and the like. In still another aspect of the present invention, there are provided kits containing compounds according to the present invention and/or compositions containing same.

6 Claims, 13 Drawing Sheets

SOLID FORMS OF AN ALPHA, OMEGA DI-SUBSTITUTED DIHYDROXY CYCLOPENTYL COMPOUND AND METHODS FOR THE PREPARATION AND USE THEREOF

CROSS-REFERENCE TO RELATED APPLICATIONS

The present application claims the benefit of U.S. provisional application 61/915,575 entitled "Solid Forms Of An Alpha, Omega DiSubstituted Dihydroxy Cyclopentenyl Compound And Methods For The Preparation And Use Thereof" filed on Dec. 13, 2013, which is incorporated herein by reference in its entirety and serves as the basis for a priority and/or benefit claim for the present application.

FIELD OF THE INVENTION

The present invention relates to solid forms of an α,ω-disubstituted dihydroxy cyclopentyl compound, and methods for the preparation and use thereof. In one aspect, the present invention relates to crystalline forms of an α,ω-disubstituted dihydroxy cyclopentyl compound, and methods for the preparation and use thereof. In another aspect, the present invention relates to substantially amorphous forms of an α,ω-disubstituted dihydroxy cyclopentyl compound, and methods for the preparation and use thereof.

BACKGROUND OF THE INVENTION

The α,ω-disubstituted dihydroxy cyclopentyl compound 7-[3α,5α-dihydroxy-2-(3α-hydroxy-5-(3-(2,5-dichloro)thienyl)-1E-pentenyl)cyclopentyl]-5Z-heptenamide:

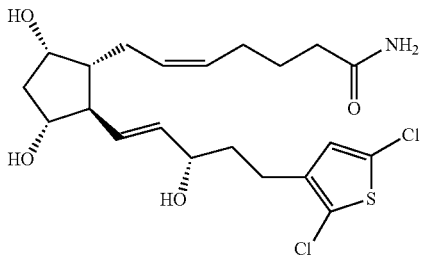 [SMILES: NC(=O)CCC/C=C\C[C@@H]1[C@@H](/C=C/[C@@H](O)CCc2cc(Cl)sc2Cl)[C@H](O)C[C@@H]1O]

is a potent ocular hypotensive particularly suited for, inter alia, the management of glaucoma (see, e.g., U.S. Pat. No. 6,602,900).

Many drug compounds exist in one or more crystalline forms, referred to as polymorphs. These polymorphs of the same molecule exhibit different physical properties, such as melting point, solubility, hardness, etc. In such cases, the danger exists of less soluble polymorphic forms precipitating from a solution made from another more soluble but less stable form. For example, the formation of crystals in an ophthalmic solution can cause serious injury to the eye. In addition, precipitation of the drug substance may cause an apparent reduction in potency and bioavailability of the product.

Accordingly, there is need for novel crystalline forms of compounds such as the α,ω-disubstituted dihydroxy cyclopentyl compound described herein.

SUMMARY OF THE INVENTION

In accordance with the present invention, there are provided multiple solid forms of an α,ω-disubstituted dihydroxy cyclopentyl compound, and methods for the preparation and use thereof. In one aspect, there are provided crystalline forms of an α,ω-disubstituted dihydroxy cyclopentyl compound, and methods for the preparation and use thereof. In another aspect, there are provided substantially amorphous forms of an α,ω-disubstituted dihydroxy cyclopentyl compound, and methods for the preparation and use thereof.

In accordance with yet another aspect of the present invention, there are provided compositions containing said α,ω-disubstituted dihydroxy cyclopentyl compound. In certain aspects, such compositions are suitable for delivery of said α,ω-disubstituted dihydroxy cyclopentyl compound to a subject in need thereof. In certain aspects, the invention relates to methods for the treatment of a variety of indications, including glaucoma, ocular hypertension, and the like.

In accordance with a further aspect of the present invention, there are provided kits containing said α,ω-disubstituted dihydroxy cyclopentyl compound and/or compositions containing same.

DETAILED DESCRIPTION OF THE INVENTION

In accordance with the present invention, there are provided solid forms of the α,ω-disubstituted dihydroxy cyclopentyl compound 7-[3α,5α-dihydroxy-2-(3α-hydroxy-5-(3-

(2,5-dichloro)thienyl)-1E-pentenyl)cyclopentyl]-5Z-heptenamide, i.e., the compound having the structure:

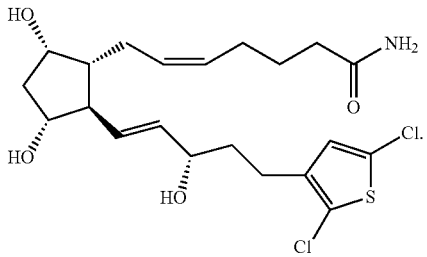 [SMILES: NC(=O)CCC/C=C\C[C@@H]1[C@@H](/C=C/[C@@H](O)CCc2cc(Cl)sc2Cl)[C@H](O)C[C@@H]1O]

In certain embodiments of the invention, the solid form of 7-[3α,5α-dihydroxy-2-(3α-hydroxy-5-(3-(2,5-dichloro)thienyl)-1E-pentenyl)cyclopentyl]-5Z-heptenamide is a crystalline anhydrate (Form A). Such crystalline forms can be further characterized by the X-ray powder diffraction (XRPD) pattern thereof. An exemplary XRPD pattern for crystalline Form A of 7-[3α,5α-dihydroxy-2-(3α-hydroxy-5-(3-(2,5-dichloro)thienyl)-1E-pentenyl)cyclopentyl]-5Z-heptenamide has at least the following peaks at about 12.01, 14.09, 20.14, 20.47 and 23.72 degrees 2θ.

Figure 1A:
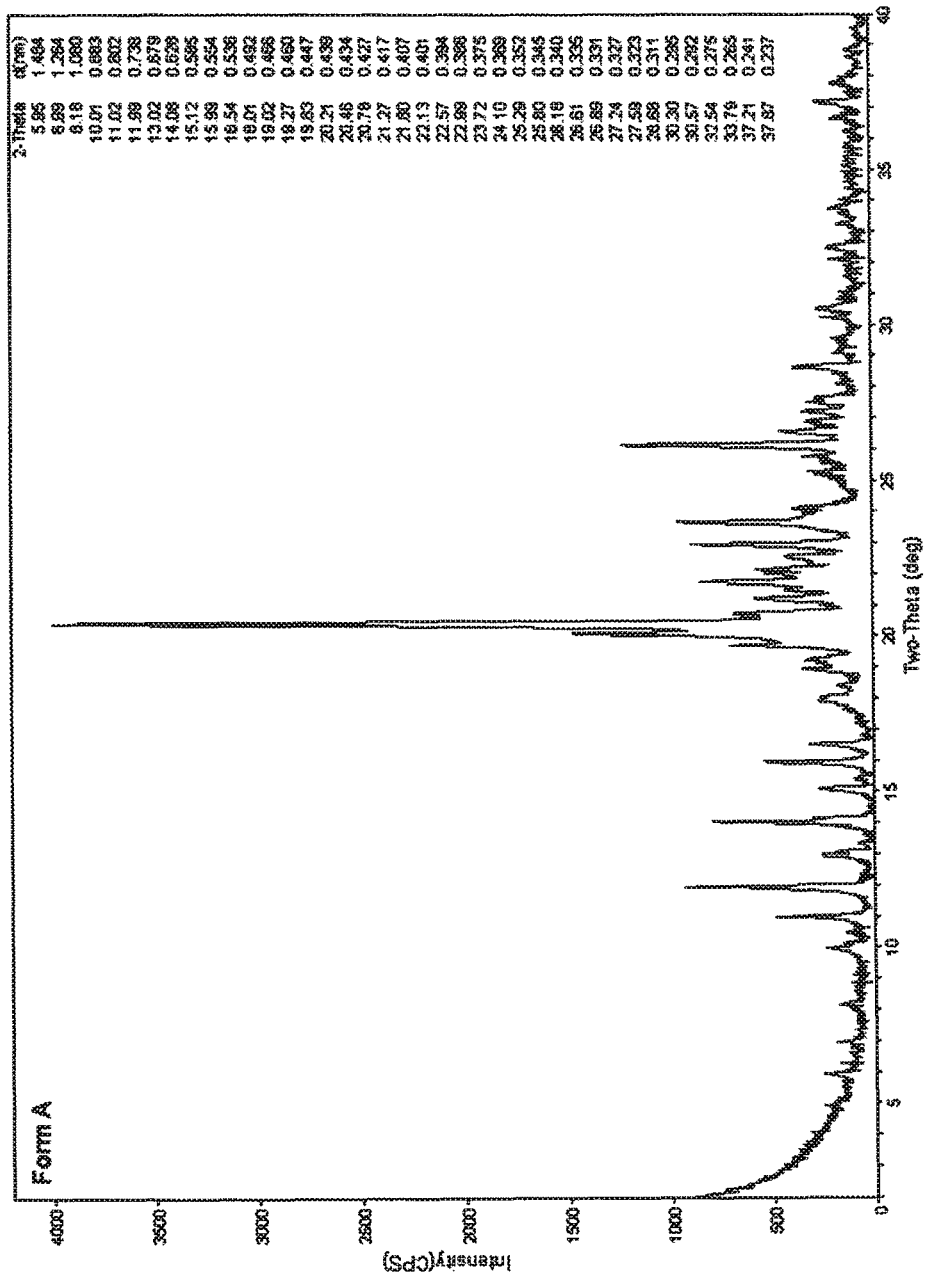
FIGS. 1A and 1C present exemplary X-ray powder diffraction (XRPD) patterns for crystalline Form A of the α,ω-disubstituted dihydroxy cyclopentyl compound described herein. Major peaks unique to Form A include peaks at about 12.01, 14.09, 20.14, 20.47 and 23.72 degrees 2θ.
Figure 1B:
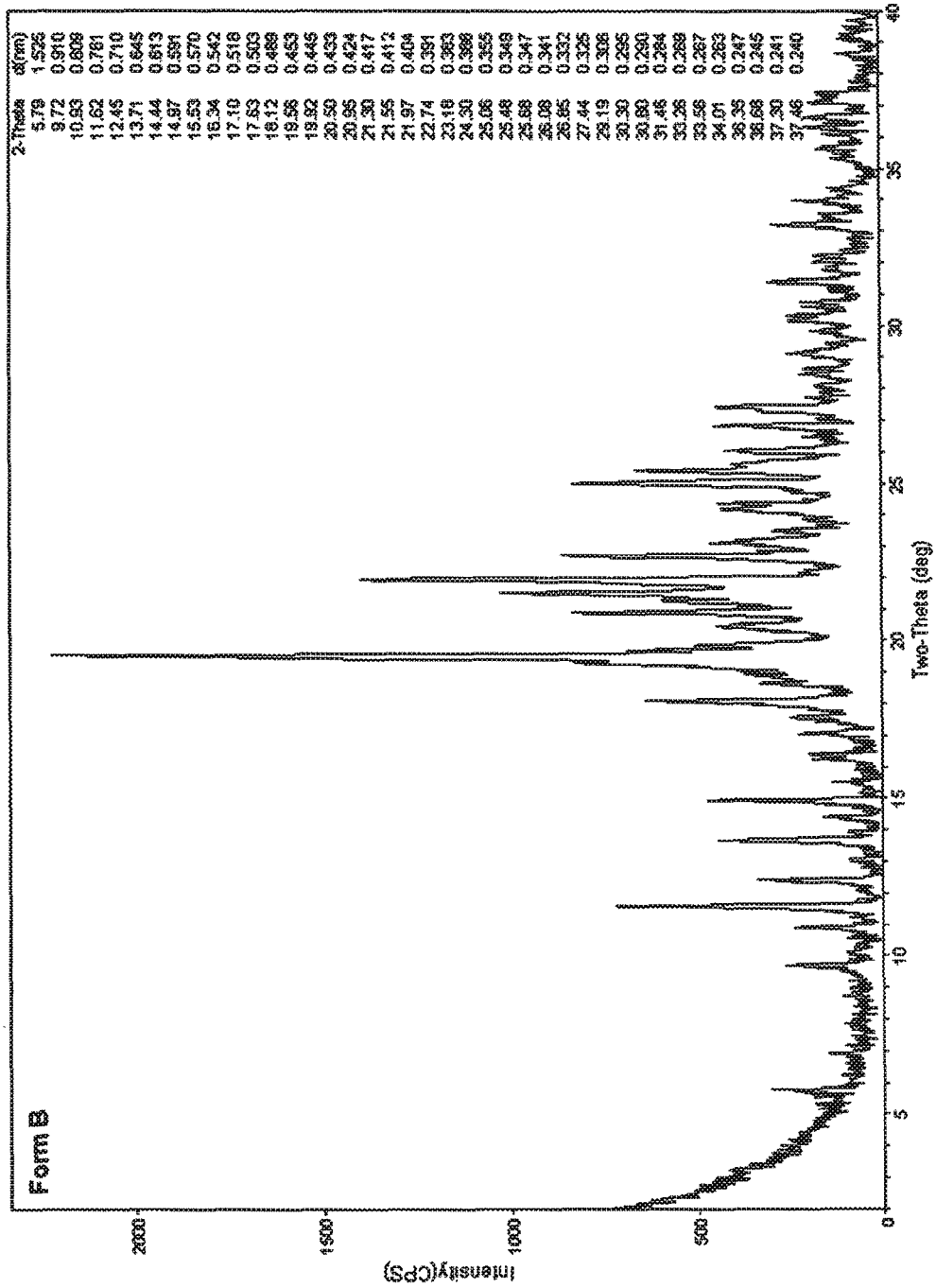
FIGS. 1B and 1D present exemplary X-ray powder diffraction (XRPD) patterns for crystalline Forms B of the α,ω-disubstituted dihydroxy cyclopentyl compound described herein. Major peaks unique to Form B include peaks at about 11.64, 19.57, 21.99, 22.74 and 25.06 degrees 2θ.
Figure 1C:
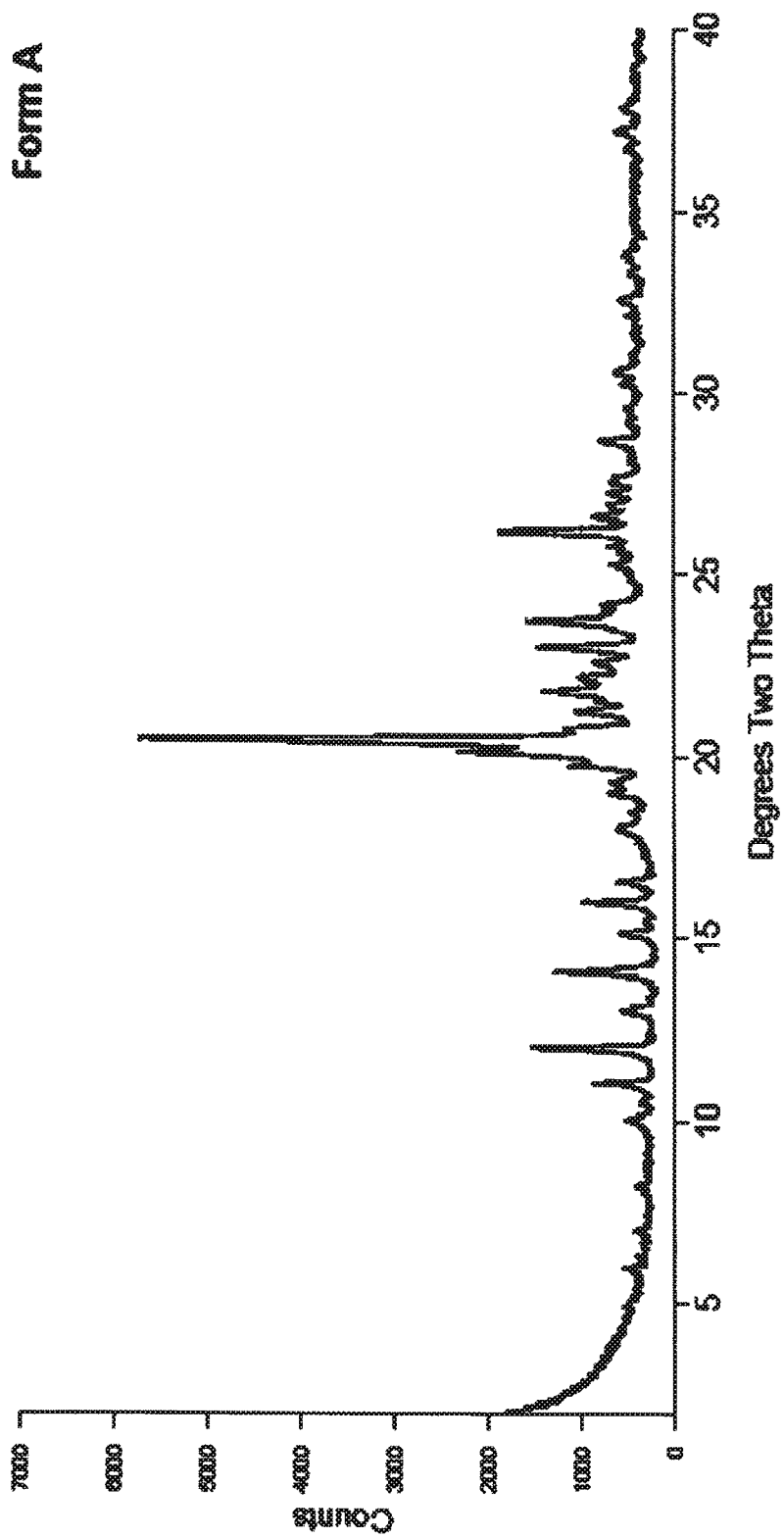

Exemplary XRPD patterns for crystalline Form A of 7-[3α,5α-dihydroxy-2-(3α-hydroxy-5-(3-(2,5-dichloro)thienyl)-1E-pentenyl)cyclopentyl]-5Z-heptenamide are substantially as shown in FIGS. 1A and 1C. A skilled person would realize that, in general, the position of the 2θ peaks in an XRPD pattern can vary by approximately 0.1, and thus exemplary peaks of the crystal form herein described would appear at about 12.01, 14.09, 20.14, 20.47 and 23.72 degrees 2θ, wherein the term "about" indicates peaks at 12.0±0.1, 14.1±0.1, 20.1±0.1, 20.5±0.1 and 23.7±0.1 degrees 2θ in an XRPD pattern. A skilled person would also understand that similar variations would apply to the other 2θ peaks in FIGS. 1A and 1C which can also vary by approximately 0.1.

In some embodiments of the present invention, crystalline Form A of 7-[3α,5α-dihydroxy-2-(3α-hydroxy-5-(3-(2,5-dichloro)thienyl)-1E-pentenyl)cyclopentyl]-5Z-heptenamide has a melting endotherm at about 62° C. and a decomposition endotherm at about 254° C.

Crystalline Form A can be further characterized as remaining substantially unchanged when maintained at a temperature in the range of about 25-40° C. under dry conditions, whereas a substantial portion thereof converts to Form B when maintained at ambient temperature and a relative humidity of about 59% for at least 72 hours. As used herein, "substantially unchanged" means that the indicia that a sample exists in crystalline Form A (e.g., the presence of the unique XRPD peaks referred to herein) remain clearly discernible. As used herein, "substantial portion thereof" refers to the major portion of the sample in question, i.e., greater than 50% of the sample, undergoes conversion from Form A to Form B; in some embodiments, greater than 60% of the sample undergoes conversion from Form A to Form B; in some embodiments, greater than 70% of the sample undergoes conversion from Form A to Form B; in some embodiments, greater than 80% of the sample undergoes conversion from Form A to Form B; in some embodiments, greater than 90% of the sample undergoes conversion from Form A to Form B.

Figure 2:
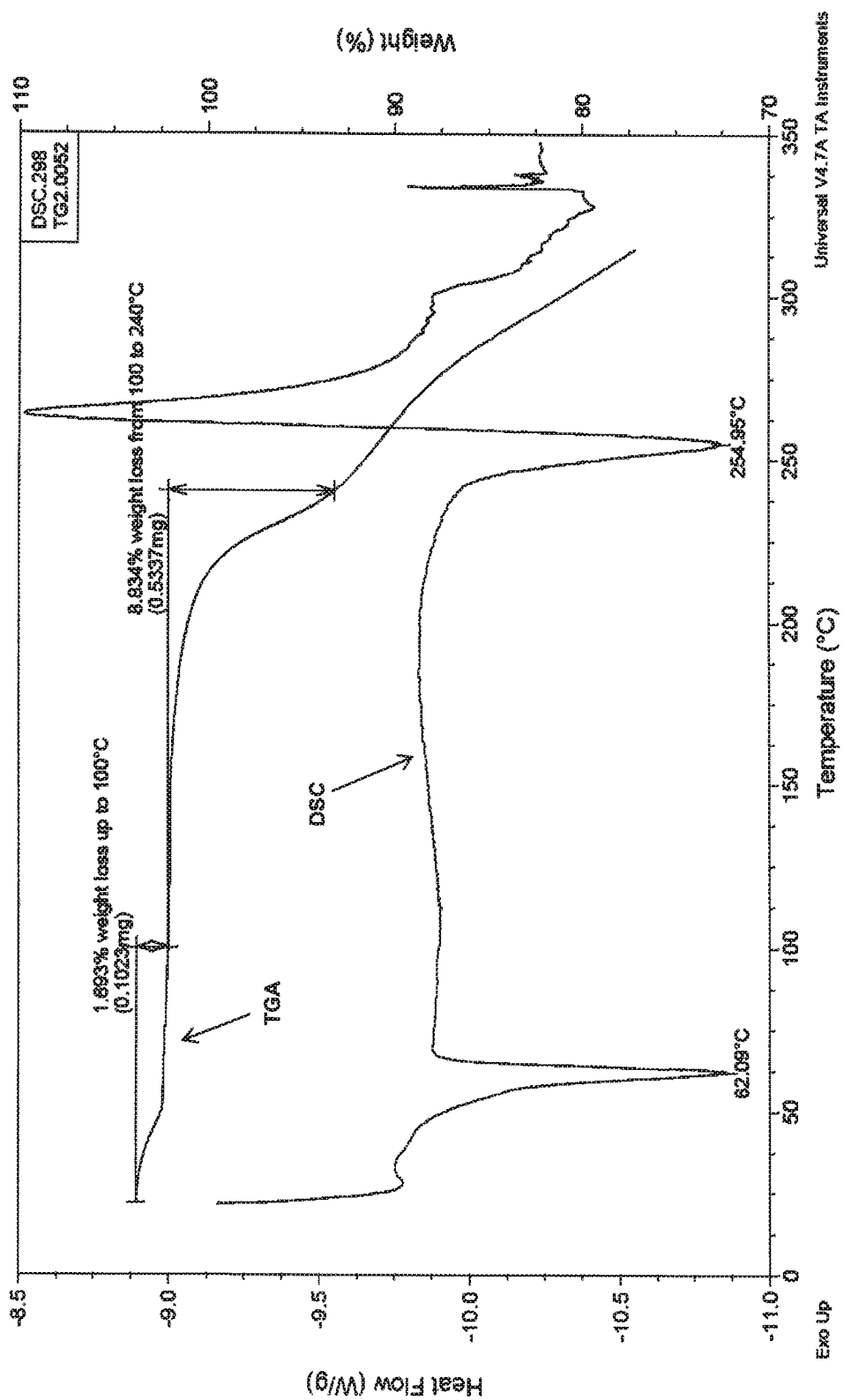
FIG. 2 presents thermogravimetric analysis/differential scanning calorimetry (TGA/DSC) curves for crystalline solid Form A of the α,ω-disubstituted dihydroxy cyclopentyl compound described herein. Melting of Form A starts at about 37° C., and ends at about 65° C. An endothermic peak at 254° C. is attributed to decomposition of the compound.

Crystalline Form A can also be characterized with reference to the differential scanning calorimetry (DSC) profile thereof; an exemplary DSC profile thereof is as shown in FIG. 2.

In some embodiments of the present invention, crystalline Form A is substantially free of other solid forms. As used herein, "substantially free" refers to samples wherein the presence of alternate solid forms falls below the detection limit, i.e., less than about 10% of said solid is in a form other than crystalline Form A.

In addition, the crystalline Form A described herein has a differential scanning calorimetry profile as shown in FIG. 2, showing melting of Form A starting at about 37° C., and ending at about 65° C., with an endothermic peak at 254° C. attributed to decomposition of the compound. This profile shows a single melting event indicating that Form A is essentially a pure crystal and does not contain any other crystalline forms. Accordingly, a skilled person would understand that the crystalline Form A described herein can be substantially free of other crystalline forms based on its DSC profile.

In certain embodiments of the present invention, the solid form of 7-[3α,5α-dihydroxy-2-(3α-hydroxy-5-(3-(2,5-dichloro)thienyl)-1E-pentenyl)cyclopentyl]-5Z-heptenamide is a crystalline hydrate (Form B). In some embodiments, the crystalline hydrate is a hemihydrate.

Figure 1D:
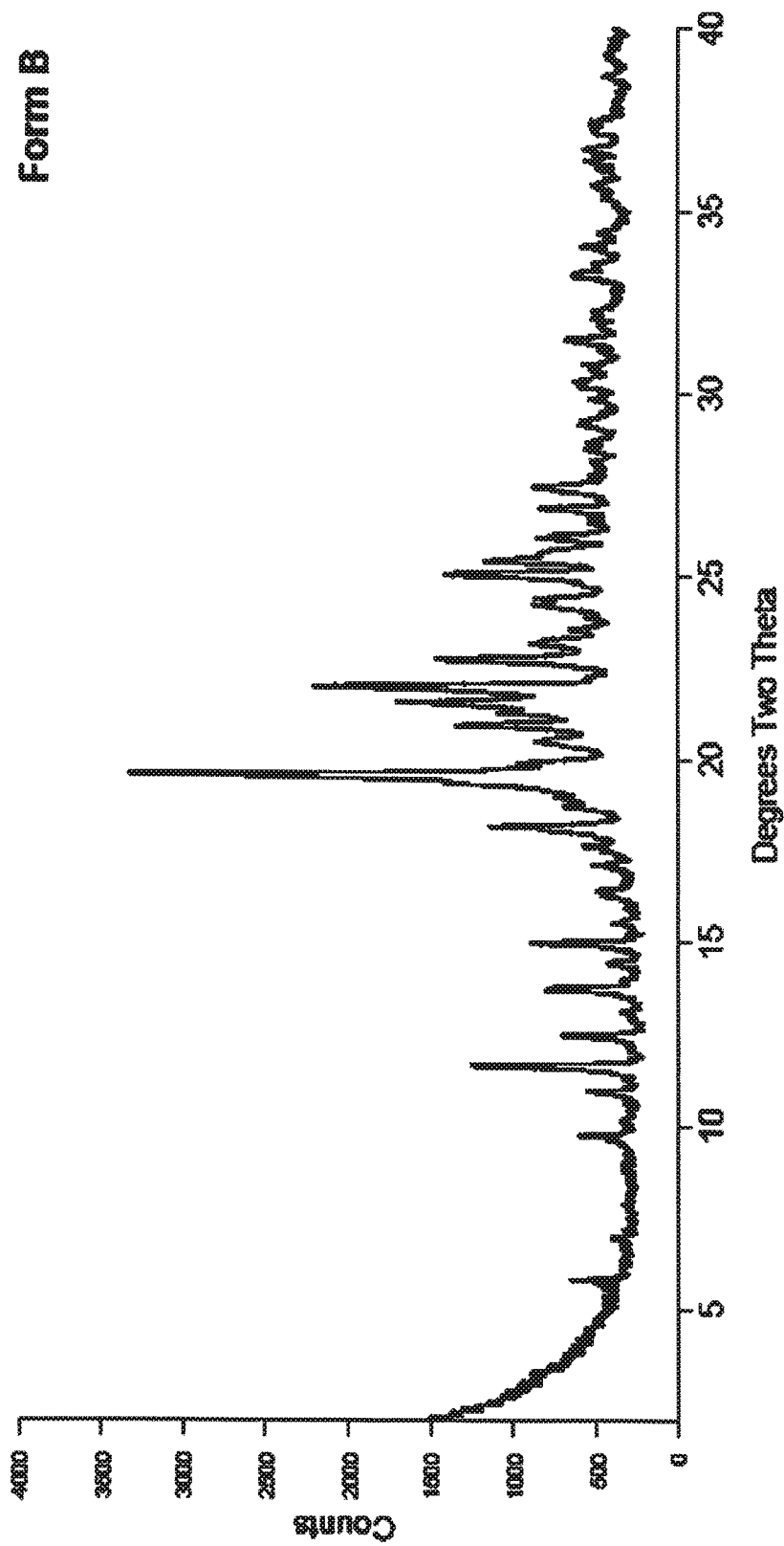

An exemplary XRPD pattern for crystalline Form B of 7-[3α,5α-dihydroxy-2-(3α-hydroxy-5-(3-(2,5-dichloro)thienyl)-1E-pentenyl)cyclopentyl]-5Z-heptenamide is substantially as shown in FIGS. 1B and 1D has peaks at least at about 11.64, 19.57, 21.99, 22.74 and 25.06 degrees 2θ.

Exemplary XRPD pattern for crystalline Form B of 7-[3α,5α-dihydroxy-2-(3α-hydroxy-5-(3-(2,5-dichloro)thienyl)-1E-pentenyl)cyclopentyl]-5Z-heptenamide are substantially as shown in FIGS. 1B and 1D. A skilled person would realize that, in general, the position of the 2θ peaks in an XRPD pattern can vary by approximately 0.1, and thus exemplary peaks of the crystal form herein described would appear at about (2θ) 11.64, 19.57, 21.99, 22.74 and 25.06, wherein the term "about" indicates peaks at (2θ) 11.6±0.1, 19.6±0.1, 22.0±0.1, 22.7±0.1 and 25.1±0.1 in an XRPD pattern. A skilled person would also understand that similar variations would apply to the other 2θ peaks in FIGS. 1B and 1D which can also vary by approximately 0.1.

In some embodiments of the present invention, crystalline Form B of 7-[3α,5α-dihydroxy-2-(3α-hydroxy-5-(3-(2,5-dichloro)thienyl)-1E-pentenyl)cyclopentyl]-5Z-heptenamide has a melting endotherm at about 50° C. and a decomposition endotherm at about 254° C.

Crystalline Form B can be further characterized as remaining substantially unchanged when maintained for up to about 1 hour at a relative humidity of about 59% and ambient temperature, or at a temperature of about 40° C. or under dry conditions, whereas a substantial portion thereof converts to amorphous form when maintained at a temperature of at least about 40° C. for at least 12 hours. As used herein, "substantially unchanged" means that the indicia that a sample exists in crystalline Form B (e.g., the presence of the unique XRPD peaks referred to herein) remain clearly discernible. As used herein, "substantial portion thereof" refers to the major portion of the sample in question, i.e., greater than 50% of the sample, undergoes conversion from Form B to the amorphous form; in some embodiments, greater than 60% of the sample undergoes conversion from Form B to the amorphous form; in some embodiments, greater than 70% of the sample undergoes conversion from Form B to the amorphous form; in some embodiments, greater than 80% of the sample undergoes conversion from Form B to the amorphous form; in some embodiments, greater than 90% of the sample undergoes conversion from Form B to the amorphous form.

Figure 3:
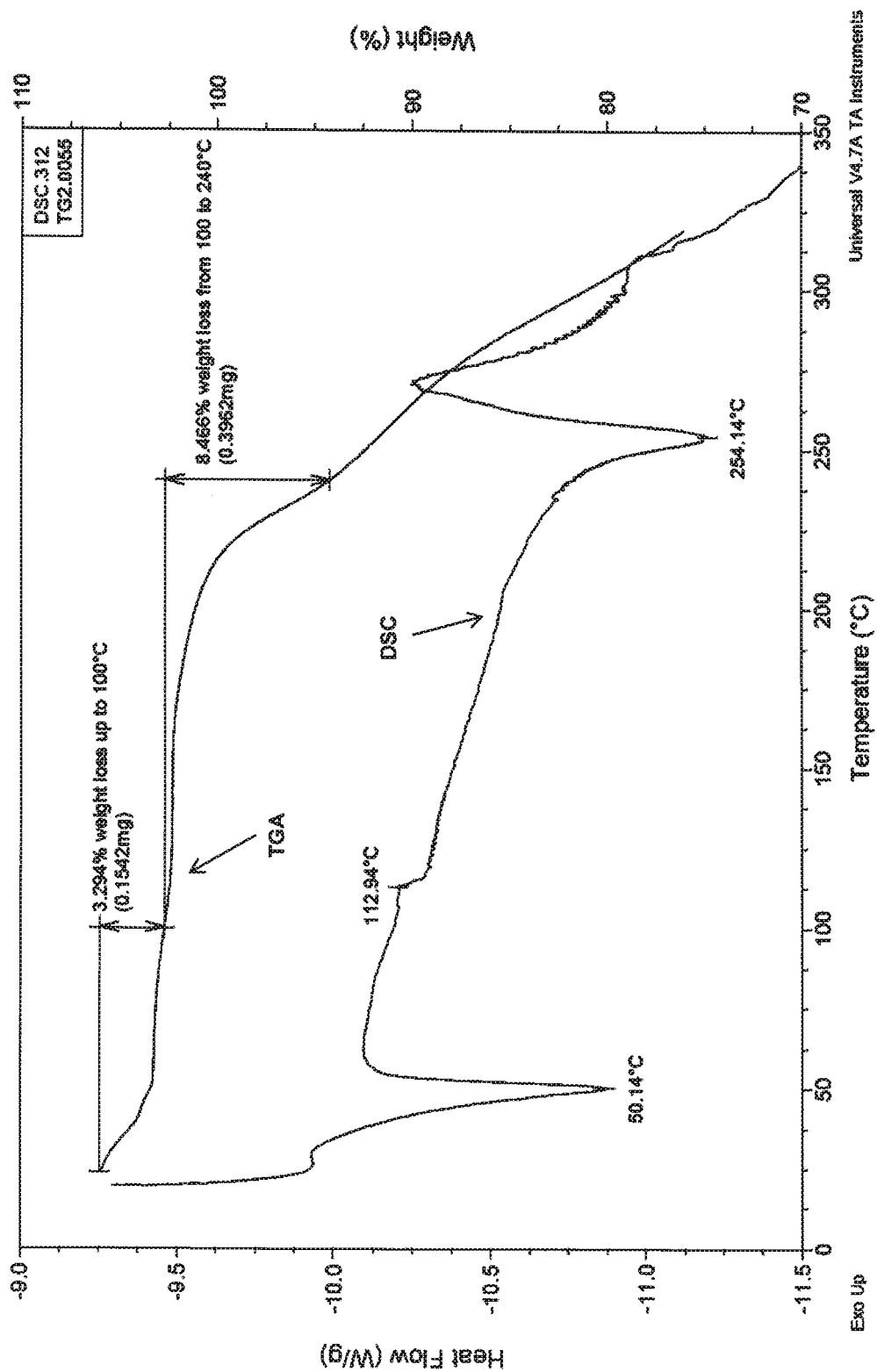
FIG. 3 presents TGA/DSC curves for crystalline solid Form B of the α,ω-disubstituted dihydroxy cyclopentyl compound described herein. Melting of Form B starts at about 25° C., and ends at about 60° C. An endothermic peak at 254° C. is attributed to decomposition of the compound.

Crystalline Form B can also be characterized with reference to the DSC profile thereof; an exemplary DSC profile thereof is as shown in FIG. 3.

In some embodiments of the present invention, crystalline Form B is substantially free of other solid forms. As used herein, "substantially free" refers to samples wherein the presence of alternate solid forms falls below the detection limit, i.e., less than about 10% of said solid is in a form other than crystalline Form B.

In addition, the crystalline Form B described herein has a differential scanning calorimetry profile as shown in FIG. 3, showing melting of Form B starting at about 25° C., and ending at about 60° C., with an endothermic peak at 254° C. attributed to decomposition of the compound. This profile shows a single melting event indicating that Form B is essentially a pure crystal and does not contain any other crystalline forms. Accordingly, a skilled person would understand that the crystalline Form B described herein can be substantially free of other crystalline forms based on its DSC profile.

In certain embodiments of the invention, the solid form of 7-[3α,5α-dihydroxy-2-(3α-hydroxy-5-(3-(2,5-dichloro)thienyl)-1E-pentenyl)cyclopentyl]-5Z-heptenamide is substantially amorphous. As used herein, "substantially amorphous" refers to samples wherein the majority of the active compound therein has no indicia of crystal structure, e.g., wherein XRPD analysis reveals no discernible peaks in an XRPD evaluation thereof.

In accordance with another embodiment of the present invention, there are provided pharmaceutical compositions comprising a therapeutically effective amount of:

crystalline Form A of 7-[3α,5α-dihydroxy-2-(3α-hydroxy-5-(3-(2,5-dichloro)thienyl)-1E-pentenyl)cyclopentyl]-5Z-heptenamide, crystalline Form B of 7-[3α,5α-dihydroxy-2-(3α-hydroxy-5-(3-(2,5-dichloro)thienyl)-1E-pentenyl)cyclopentyl]-5Z-heptenamide, a substantially amorphous form of 7-[3α,5α-dihydroxy-2-(3α-hydroxy-5-(3-(2,5-dichloro)thienyl)-1E-pentenyl)cyclopentyl]-5Z-heptenamide, or combinations of any two or more thereof, in an ophthalmically acceptable carrier therefore.

Those skilled in the art can readily identify ophthalmically acceptable carriers suitable for administration (or the manufacture of medicaments containing) the α,ω-disubstituted dihydroxy cyclopentyl compounds disclosed herein. Specifically, a drug to be administered systemically may be confected as a solution, emulsion, suspension, aerosol, or the like.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions according to the present invention include, but are not limited to, benzalkonium chloride, chlorobutanol, thimerosal, phenylmercuric acetate, phenylmercuric nitrate, and the like. A useful surfactant is, for example, Tween 80. Likewise, various useful vehicles may be used in the ophthalmic preparations according to the present invention. These vehicles include, but are not limited to, polyvinyl alcohol, povidone, hydroxypropyl methyl cellulose, poloxamers, carboxymethyl cellulose, hydroxyethyl cellulose, purified water, and the like.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers including acetate buffers, citrate buffers, phosphate buffers, borate buffers, and the like, are contemplated for use herein. Acids or bases may be used to adjust the pH of these formulations as needed.

In a similar vein, an ophthalmically acceptable antioxidant for use in accordance with the present invention includes, but is not limited to, sodium metabisulfite, sodium thiosulfate, acetylcysteine, butylated hydroxyanisole, butylated hydroxytoluene, and the like.

Other excipient components which may be included in the ophthalmic preparations contemplated herein are chelating agents. A useful chelating agent is edetate disodium, although other chelating agents may also be used in place of, or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

The amount of the α,ω-disubstituted dihydroxy cyclopentyl compound administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. Therapeutically effective dosages contemplated for α,ω-disubstituted dihydroxy cyclopentyl compounds according to the present invention may be in the range of about 0.5 or about 1 to about 100 mg/kg/day.

In one embodiment of the present invention, compositions described herein are packaged in a dropper for ophthalmic application.

Compounds according to the present invention are useful for the treatment of a variety of indications, e.g., inflammatory eye conditions (e.g., dry eye disease, conjunctivitis, and the like), glaucoma, and the like.

In accordance with one aspect of the present invention, use of compounds according to the invention in the treatment and/or prevention, and/or in the manufacture of a medicament for the treatment and/or prevention, of any of the above-referenced diseases and/or conditions is also contemplated.

Therefore, in accordance with yet another embodiment of the present invention, there are provided methods for reducing ocular hypertension comprising administering to a subject in need thereof a therapeutically effective amount of a composition as described herein.

In accordance with still another embodiment of the present invention, there are provided methods for treating glaucoma comprising administering to a subject in need thereof a therapeutically effective amount of a composition as described herein.

In one embodiment of the above-referenced methods, the compositions according to the present invention are administered via topical administration to an eye.

"Treatment," "treat," or any other form of these words as used herein are intended to mean use in the diagnosis, cure, mitigation, treatment, or prevention of disease in man or other animals.

In accordance with yet another embodiment of the present invention, there are provided methods for preparing defined solid forms of the compound 7-[3α,5α-dihydroxy-2-(3α-hydroxy-5-(3-(2,5-dichloro)thienyl)-1E-pentenyl)cyclopentyl]-5Z-heptenamide employing one or more of the following crystallization techniques, e.g., evaporation, cooling, slurry, vapor diffusion, and the like.

In accordance with a further embodiment of the present invention, there are provided methods for preparing Form A of the compound 7-[3α,5α-dihydroxy-2-(3α-hydroxy-5-(3-(2,5-dichloro)thienyl)-1E-pentenyl)cyclopentyl]-5Z-heptenamide from the amorphous state thereof, said method comprising:
 (a) suspending and/or dissolving said compound in a suitable diluent,
 (b) subjecting the resulting suspension and/or solution to:
  (i) conditions suitable for evaporation of diluent therefrom, and thereafter triturating the resulting oil with a suitable non-polar solvent,
  (ii) gradually reducing the temperature thereof, and
  (iii)(a) storing a suspension thereof at room temperature for a time sufficient for crystals of said compound to form, or (b) gradually adding sufficient non-solvent thereto to promote precipitation of said compound therefrom.

As used herein, "suitable diluent" refers to media in which the compound 7-[3α,5α-dihydroxy-2-(3α-hydroxy-5-(3-(2,5-dichloro)thienyl)-1E-pentenyl)cyclopentyl]-5Z-heptenamide can be suspended and/or dissolved. Exemplary diluents include ketones (e.g., acetone, methyl ethyl ketone, and the like), alcohols (e.g., methanol, ethanol, propanol, butanol, and the like), esters (e.g., ethyl acetate), nitriles (e.g., acetonitrile), ethers (e.g., diethyl ether, methyl tert-butyl ether, tetrahydrofuran, 2-methyltetrahydrofuran, dioxane, and the like), alkanes (e.g., hexane, heptane, and the like), chlorinated hydrocarbons (e.g., dichloromethane, chloroform, and the like), aromatics (e.g., benzene, toluene, and the like), as well as mixtures of any two or more thereof.

As used herein, "conditions suitable for evaporation of diluent therefrom" refers to the combination of temperature and/or atmosphere that promotes removal of diluent from a suspension or solution. For example, elevated temperatures at atmospheric pressure can be employed; alternatively, ambient temperature can be employed at reduced pressures; or the combination of elevated temperature and reduced pressure can be employed to promote evaporation of diluent from a suspension or solution containing an α,ω-disubstituted dihydroxy cyclopentyl compound according to the present invention.

As used herein, "suitable non-polar solvent" refers to a solvent of sufficiently low polarity to induce crystal formation of a polar compound such as the compound 7-[3α,5α-dihydroxy-2-(3α-hydroxy-5-(3-(2,5-dichloro)thienyl)-1E-pentenyl)cyclopentyl]-5Z-heptenamide, e.g., an ether.

As used herein, "time sufficient for crystals . . . to form" refers to the amount of time required for a given sample to equilibrate into the solid form preferred under the particular conditions. The amount of time required to do so can vary from minutes to days; typically 1-14 days is adequate for such purpose.

As used herein, "non-solvent" refers to medium in which the compound 7-[3α,5α-dihydroxy-2-(3α-hydroxy-5-(3-(2,5-dichloro)thienyl)-1E-pentenyl)cyclopentyl]-5Z-heptenamide is not appreciably soluble; therefore, the use of "sufficient" non-solvent contemplates the addition of a quantity of non-solvent sufficient to induce precipitation and/or crystallization of the majority of said compound from a solution or suspension containing same.

In accordance with a further embodiment of the present invention, there are provided methods for preparing Form B of the compound 7-[3α,5α-dihydroxy-2-(3α-hydroxy-5-(3-(2,5-dichloro)thienyl)-1E-pentenyl)cyclopentyl]-5Z-heptenamide from the amorphous state, said method comprising:
 (a) suspending and/or dissolving said compound in a suitable diluent,
 (b) subjecting the resulting suspension and/or solution to:
  (i) conditions suitable for evaporation of diluent therefrom, and thereafter triturating the resulting oil with a suitable polar solvent,
  (ii) gradually reducing the temperature thereof, and
  (iii)(a) storing a suspension thereof at room temperature for a time sufficient for crystals of said compound to form, or (b) gradually adding sufficient non-solvent thereto to promote precipitation of said compound therefrom.

In accordance with a further embodiment of the present invention, there are provided methods for converting Form A of the compound 7-[3α,5α-dihydroxy-2-(3α-hydroxy-5-(3-(2,5-dichloro)thienyl)-1E-pentenyl)cyclopentyl]-5Z-heptenamide into Form B thereof, said method comprising subjecting Form A of said compound to a relative humidity of about 59% at ambient temperature for at least 72 hours.

In accordance with another aspect of the present invention, there are provided kits comprising the compositions described herein, a container, and instructions for administration of said composition to a subject in need thereof for the mitigation of glaucoma, ocular hypertension, or the like.

The actual dose of the active compounds of the present invention depends on the specific compound, and on the condition to be treated; the selection of the appropriate dose is well within the knowledge of the skilled artisan.

For treatment of diseases affecting the eye including glaucoma, these compounds can be administered topically, periocularly, intraocularly, or by any other effective means known in the art.

For the treatment of glaucoma, combination treatment with the following classes of drugs is contemplated:
 β-Blockers (or β-adrenergic antagonists) including carteolol, levobunolol, metipranolol, timolol hemihydrate, timolol maleate, β1-selective antagonists such as betaxolol, and the like, or pharmaceutically acceptable salts or prodrugs thereof;
 Adrenergic Agonists including
  non-selective adrenergic agonists such as epinephrine borate, epinephrine hydrochloride, and dipivefrin, and the like, or pharmaceutically acceptable salts or prodrugs thereof; and α₂-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including direct acting cholinergic agonists such as charbachol, pilocarpine hydrochloride, pilocarbine nitrate, pilocarpine, and the like, or pharmaceutically acceptable salts or prodrugs thereof;

chlolinesterase inhibitors such as demecarium, echothiophate, physostigmine, and the like, or pharmaceutically acceptable salts or prodrugs thereof;

Glutamate Antagonists such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and Prostaglandins including travoprost, UFO-21, chloprostenol, fluprostenol, 13,14-dihydro-chloprostenol, latanoprost and the like.

EXAMPLES

Various aspects of the present invention are illustrated by the following non-limiting examples. The examples are for illustrative purposes and are not a limitation on any practice of the present invention. It will be understood that variations and modifications can be made without departing from the spirit and scope of the invention. One of ordinary skill in the art readily knows how to synthesize or commercially obtain the reagents and components described herein.

X-Ray powder diffraction patterns (XRPD) were obtained for the crystalline form described herein under the following conditions:

Equipment: Rigaku Smart-Lab
Scan range: 2 to 40° (2θ)
Scan speed: 3° (2θ) per minute
Step width: 0.02° (2θ)
X-ray information: Cu Kα, λ=1.54 Å, 40 kV/44 mA Approximately 5-10 mg of the sample was gently applied on a low background Si holder and subjected to XRPD scanning.

Differential scanning calorimetry was performed by loading 2 to 6 mg material in a standard, crimped, aluminum DSC sample pan and then subjecting the sample to a heat ramp from 20 to 350° C. at a rate of 10° C. per min.

The compound 7-[3α,5α-dihydroxy-2-(3α-hydroxy-5-(3-(2,5-dichloro)thienyl)-1E-pentenyl)cyclopentyl]-5Z-heptenamide described herein can by synthesized according to the procedures in U.S. Pat. No. 6,602,900.

Example 1

The compound 7-[3α,5α-dihydroxy-2-(3α-hydroxy-5-(3-(2,5-dichloro)thienyl)-1E-pentenyl)cyclopentyl]-5Z-heptenamide is dissolved in a suitable solvent such as acetonitrile, dichloromethane, ethanol, ethyl acetate, 2-methyltetrahydrofuran, 1-propanol, or a mixture of toluene and methanol (v/v 25/1). Evaporation of the solvent therefrom followed by trituration of the resulting oil with diethyl ether provided crystalline Form A, as determined by XRPD.

Alternatively, trituration of the resulting oil with acetonitrile provided crystalline Form B, as determined by XRPD.

Example 2

A warm solution of the compound 7-[3α,5α-dihydroxy-2-(3α-hydroxy-5-(3-(2,5-dichloro)thienyl)-1E-pentenyl)cyclopentyl]-5Z-heptenamide was prepared in a variety of solvents, then allowed to slowly cool until crystals were observed. The combination of solvents/cooling conditions which facilitated formation of crystalline Form A is summarized in Table 1:

TABLE 1

| Solvent | Conditions |
| --- | --- |
| Acetonitrile | 95° C. → room temperature |
| Acetonitrile (dry) | 80° C. → room temperature |
| Ethyl acetate | 90° C. → room temperature |
| Ethyl acetate (dry) | 80° C. → room temperature |
| Acetone/hexane (v/v 1/1.4) | 75° C. → room temperature |
| 2-propanol/diethyl ether (v/v 1/5) | Room temperature → −20° C. |
| Methyl ethyl ketone/hexane (v/v 7/10; dry) | 80° C. → room temperature |

The combination of solvents/cooling conditions which facilitated formation of crystalline Form B is summarized in Table 2:

TABLE 2

| Solvent | Conditions |
| --- | --- |
| Dioxane/methyl tert-butyl ether (v/v 1/4) | Room temperature → −20° C. |
| 2-methyltetrahydrofuran/hexane (v/v 3/2) | Room temperature → 5° C. |
| 2-methyltetrahydrofuran/hexane (v/v 7/5) | 70° C. → room temperature |

As shown in Tables 1 and 2, the crystalline form of the compound 7-[3α,5α-dihydroxy-2-(3α-hydroxy-5-(3-(2,5-dichloro)thienyl)-1E-pentenyl)cyclopentyl]-5Z-heptenamide can be controlled by the choice of solvent from which the compound is precipitated, and the temperatures employed to induce crystallization.

Example 3

A slurry of the compound 7-[3α,5α-dihydroxy-2-(3α-hydroxy-5-(3-(2,5-dichloro)thienyl)-1E-pentenyl)cyclopentyl]-5Z-heptenamide was prepared in a variety of media, then allowed to stand at room temperature for a time sufficient to allow crystals to form. The diluents which facilitated formation of crystalline Form A are summarized in Table 3:

TABLE 3

| Diluent | Crystallization time, days |
| --- | --- |
| Acetone (dry) | 3 |
| Acetonitrile (dry) | 3 |
| Diethyl ether | 4 |
| Ethyl acetate | 5 |
| 1-butanol/methyl tert-butyl ether (v/v 1/20; dry) | 3 |
| Dioxane/methyl tert-butyl ether (v/v 1/4; dry) | 3 |
| Ethanol/toluene (v/v 1/40; dry) | 3 |
| Methanol/diethyl ether (v/v1/10) | 12 |

TABLE 3-continued

| Diluent | Crystallization time, days |
|---|---|
| Methanol/diethyl ether (v/v1/20) | 5 |
| Methyl ethyl ketone/heptane (v/v 1/1; dry) | 3 |
| 2-methyltetrahydrofuran/hexane (v/v1/1) | 7 |
| 2-methyltetrahydrofuran/hexane (v/v1/1; dry) | 3 |
| Tetrahydrofuran/hexane (v/vl/1; dry) | 3 |
| Toluene (dry) | 3 |

The diluents which facilitated formation of crystalline Form B are summarized in Table 4:

TABLE 4

| Diluent | Crystallization time, days |
|---|---|
| Diethyl ether (wet) | 4 |
| Methyl ethyl ketone | 5 |
| 1-butanol/methyl tert-butyl ether (v/v 1/20) | 4 |
| 1-butanol/methyl tert-butyl ether (v/v 1/20; wet) | 6 |
| Dioxane/methyl tert-butyl ether (v/v 1/4) | 7 |
| Ethanol/toluene (v/v 1/40) | 7 |
| Methyl ethyl ketone (v/v 1/1) | 5 |
| Tetrahydrofuran/hexane (v/v 1/2) | 4 |
| Toluene | 5 |

As shown in Tables 3 and 4, the crystalline form of the compound 7-[3α,5α-dihydroxy-2-(3α-hydroxy-5-(3-(2,5-dichloro)thienyl)-1E-pentenyl)cyclopentyl]-5Z-heptenamide can be controlled by the choice of diluent from which the compound is crystallized using slurry crystallization methods.

Example 4

The compound 7-[3α,5α-dihydroxy-2-(3α-hydroxy-5-(3-(2,5-dichloro)thienyl)-1E-pentenyl)cyclopentyl]-5Z-heptenamide can also be crystallized employing vapor diffusion techniques. Crystalline Form A can be obtained when said compound is dissolved in a polar solvent such as acetonitrile, and then exposed to a non-polar solvent such as toluene at room temperature.

Alternatively, crystalline Form B can be obtained when said compound is dissolved in a polar solvent such as acetone, and then exposed to a non-aromatic, non-polar solvent such as hexane at room temperature.

Example 5

The compound 7-[3α,5α-dihydroxy-2-(3α-hydroxy-5-(3-(2,5-dichloro)thienyl)-1E-pentenyl)cyclopentyl]-5Z-heptenamide can be prepared in substantially amorphous form by exposing said compound to a temperature of at least about 40° C. for at least 12 hours.

Example 6

Figure 4A:
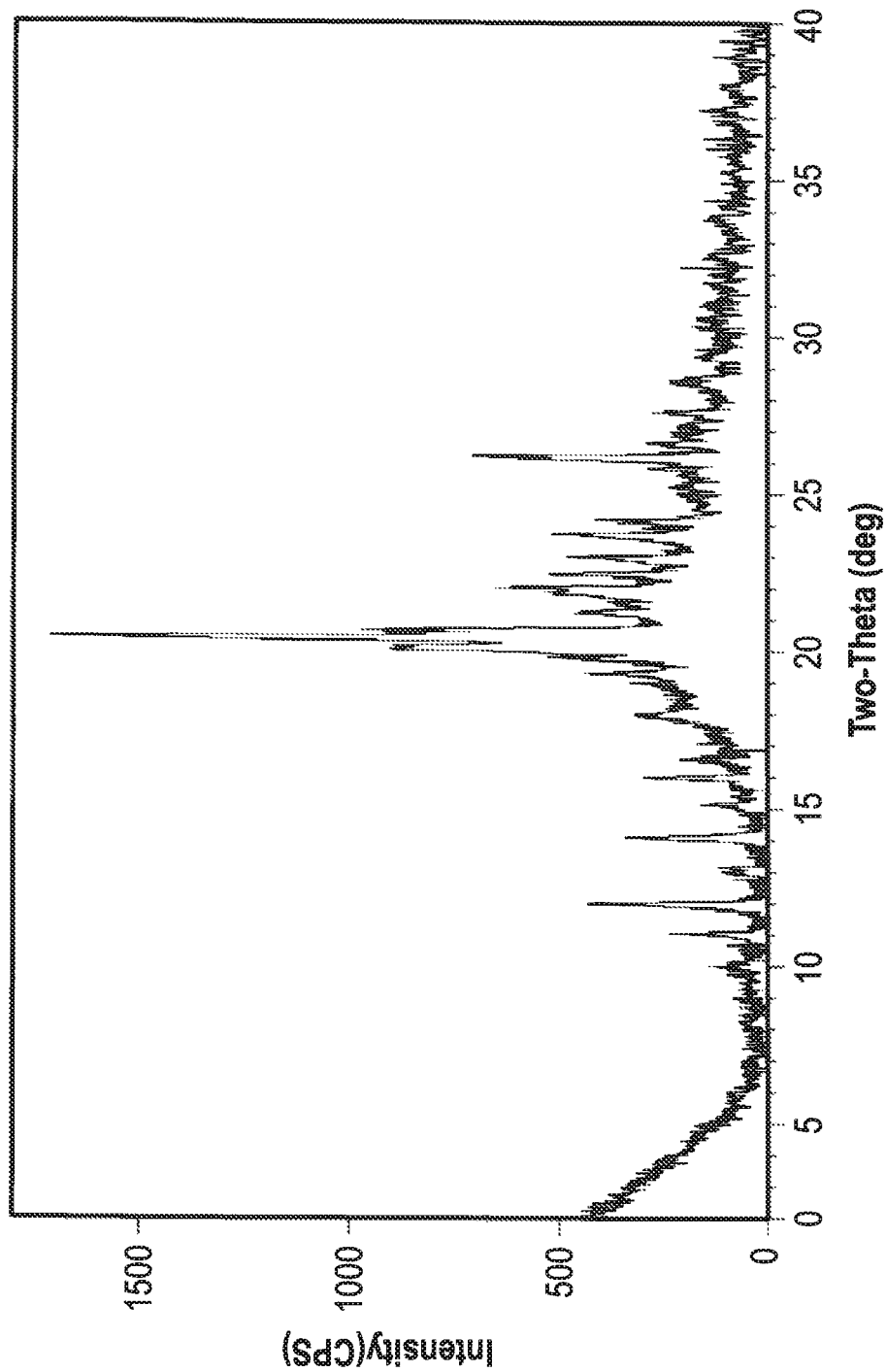
FIG. 4A presents an XRPD pattern of a sample of crystalline Form A after being maintained at 22±2° C. and relative humidity of 0% for 144 hours.
Figure 4B:
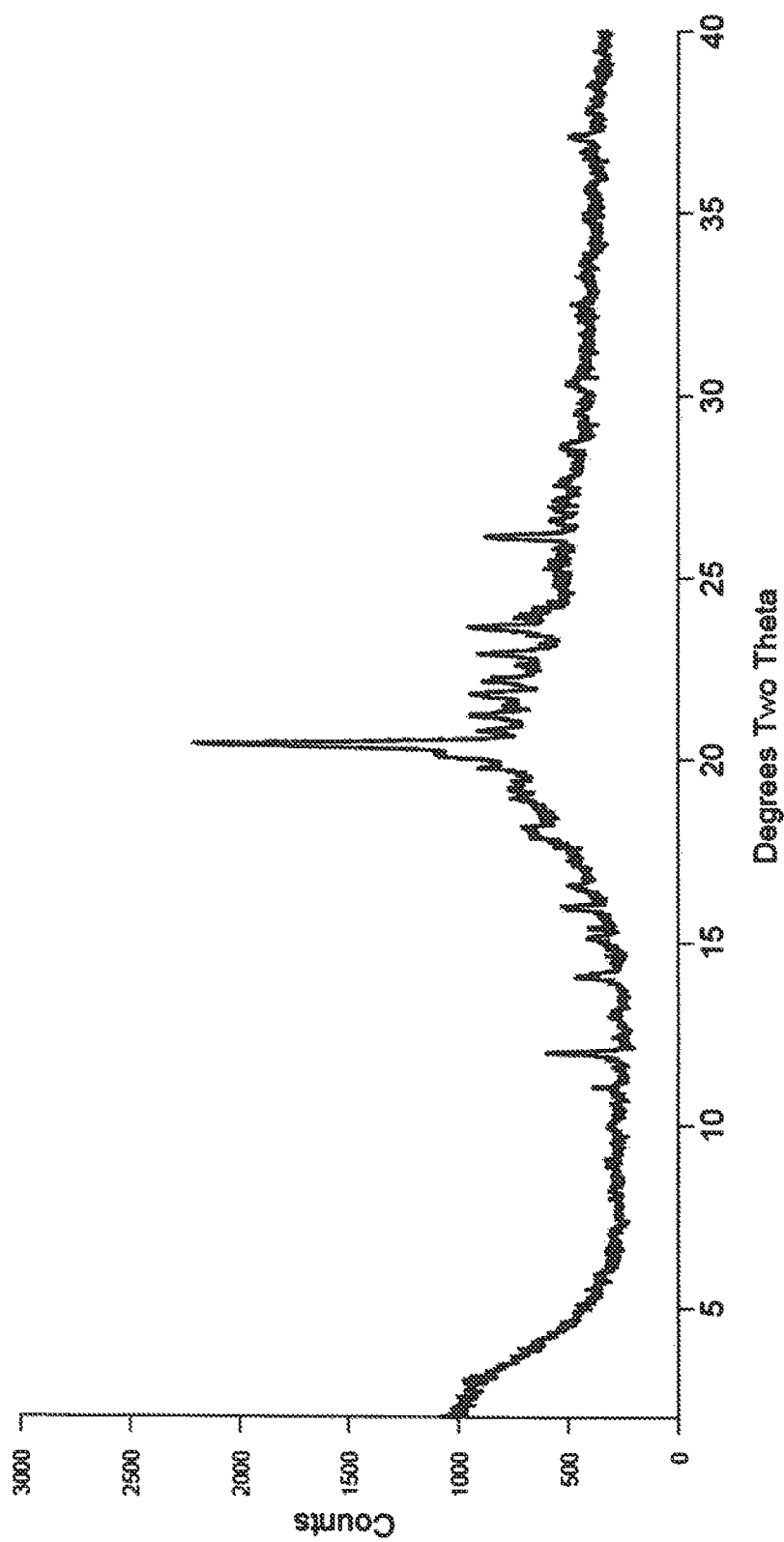
FIG. 4B presents an XRPD pattern of a sample of crystalline Form A after being maintained at 40° C. for 25 minutes.

A sample of 5-10 milligrams of crystalline Form A was maintained at a temperature of 22±2° C. and relative humidity of 0% for 144 hours When the XRPD spectrum of the sample after being maintained at 22±2° C. and relative humidity of 0% for 144 hours (see FIG. 4A) was compared to the XRPD spectrum of the sample before being maintained under those conditions, no significant change was observed in the XRPD spectrum in that the peaks at about 12.01, 14.09, 20.14, 20.47 and 23.72 degrees 2θ were still present, indicating that crystal Form A had remained substantially unchanged. A similar lack of significant change in the XRPD pattern was also observed when a sample was stored at 40° C. for 25 minutes (see FIG. 4B).

Figure 5:
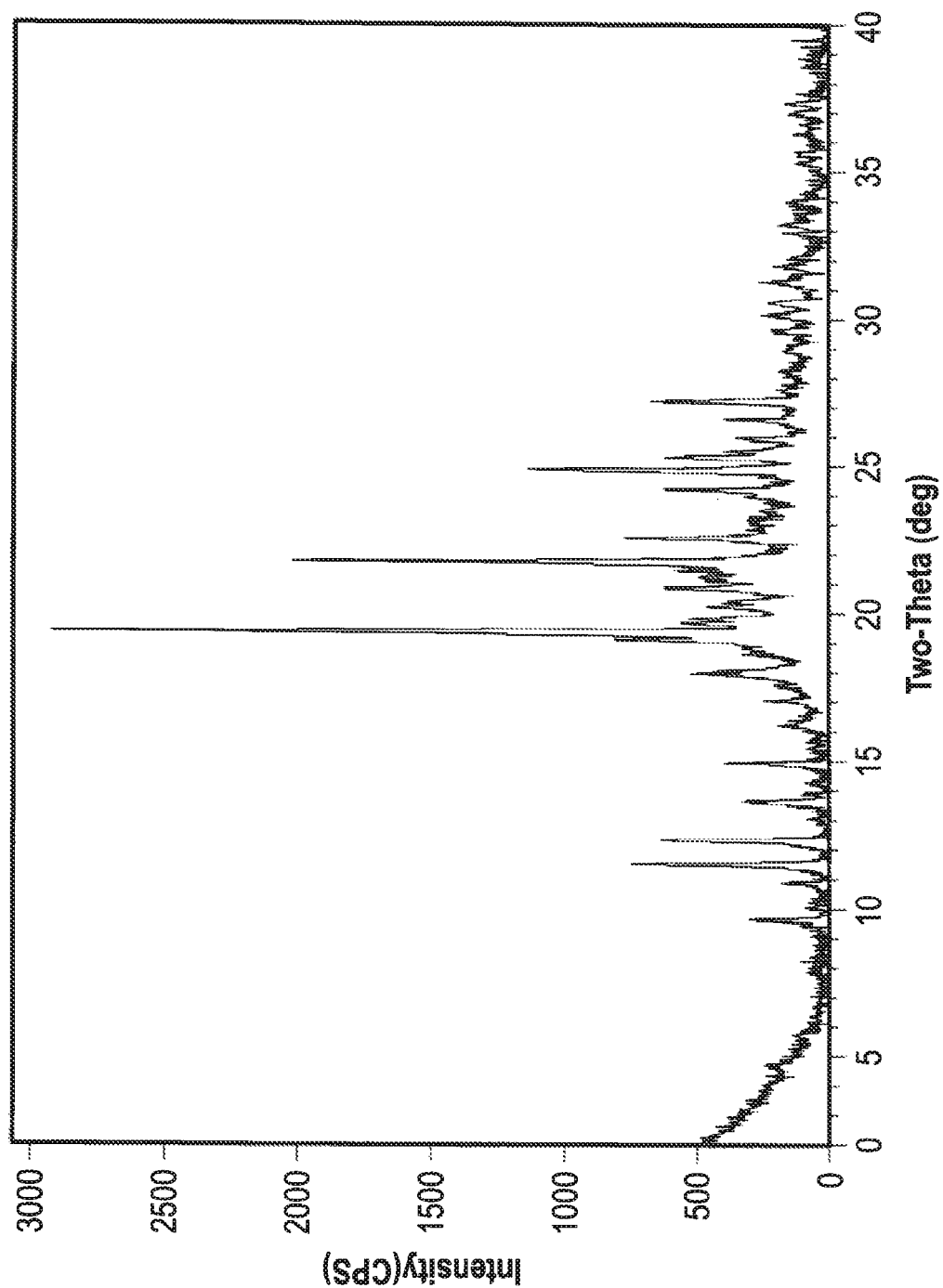
FIG. 5 presents an XRPD pattern of a sample of crystalline Form A after being maintained at 22±2° C. and relative humidity of 59% for 144 hours.

In addition, another sample of 5-10 milligrams of crystalline Form A was maintained at a temperature of 22±2° C. and relative humidity of 59% for 144 hours. When the XRPD spectrum of the sample after being maintained at 22±2° C. and relative humidity of 59% for 144 hours (see FIG. 5) was compared to the XRPD spectrum of the sample before being maintained under those conditions, the XRPD spectrum revealed the presence of peaks at about 11.64, 19.57, 21.99, 22.74 and 25.06 degrees 2θ, indicating that a substantial portion of crystalline Form A had converted to crystalline Form B.

Example 7

Figure 6A:
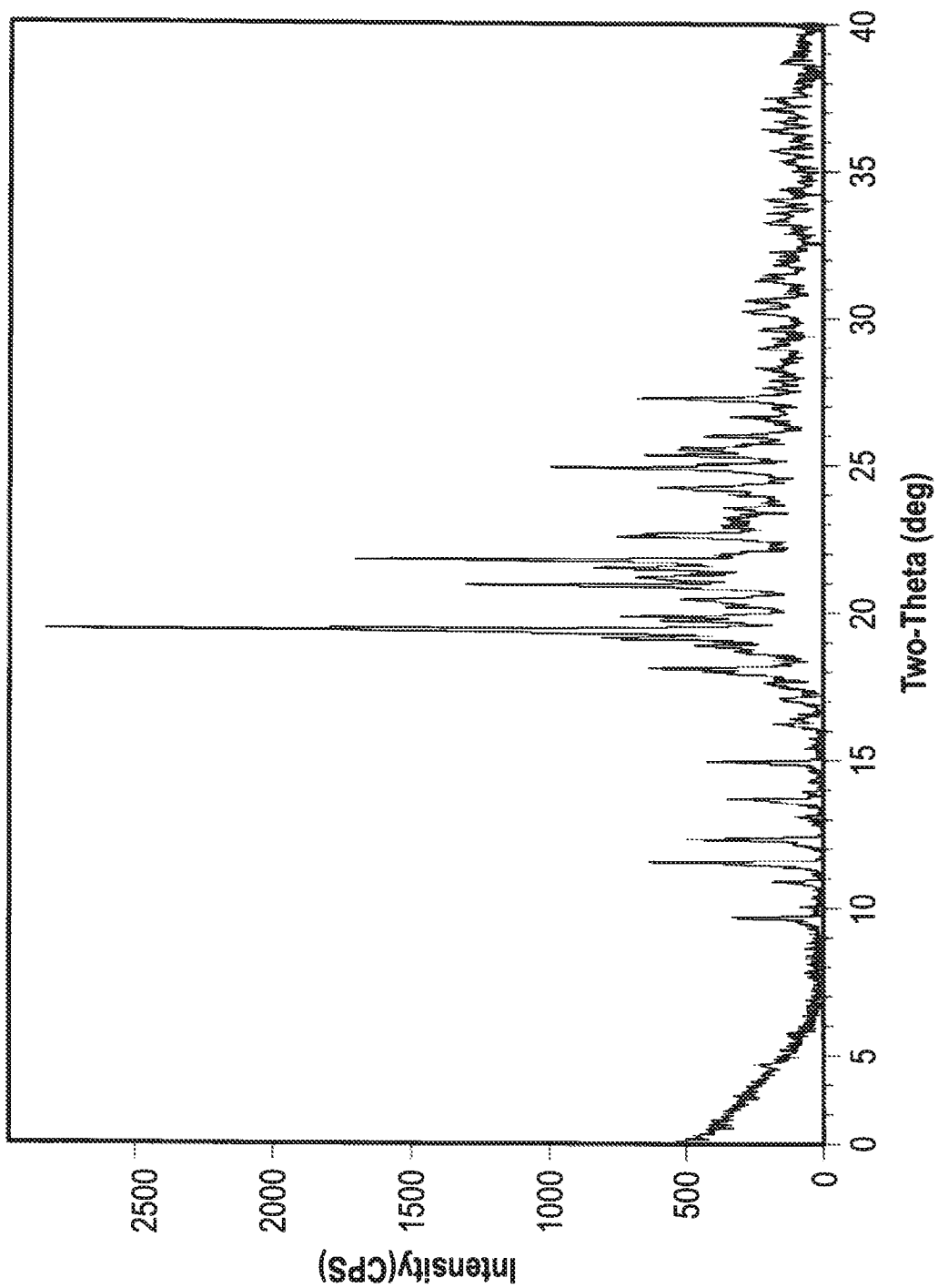
FIG. 6A presents an XRPD pattern of a sample of crystalline Form B after being maintained at 22±2° C. and relative humidity of 59% for 120 hours.
Figure 6B:
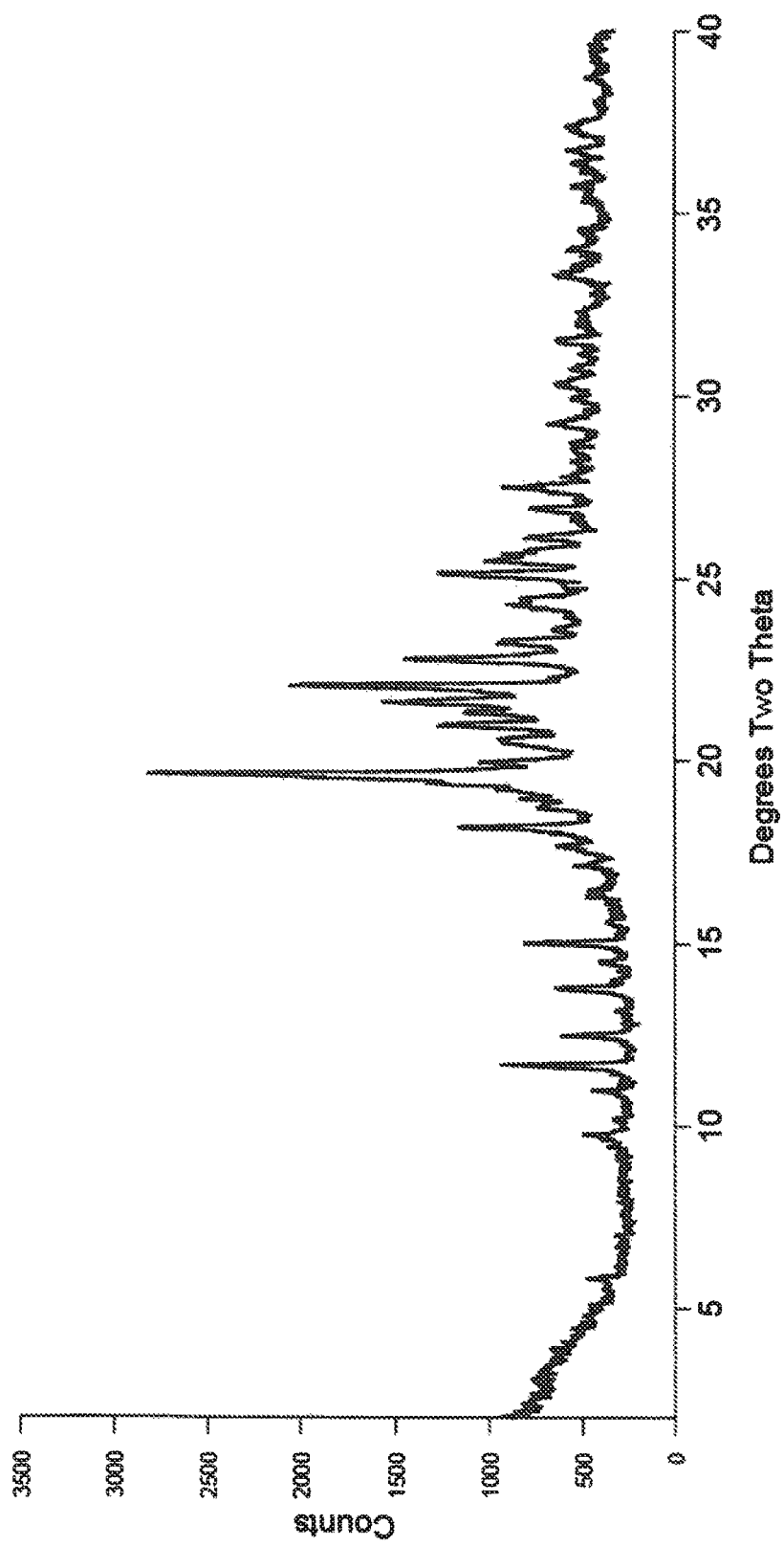
FIG. 6B presents an XRPD pattern of a sample of crystalline Form B after being maintained at 40° C. for 25 minutes.

A sample of 5-10 milligrams of crystalline Form B was maintained at a temperature of 22±2° C. and relative humidity of 59% for 120 hours. When the XRPD spectrum of the sample after being maintained at 22±2° C. and relative humidity of 59% for 120 hours (see FIG. 6A) was compared to the XRPD spectrum of the sample before being maintained under those conditions, no significant change was observed in the XRPD spectrum in that the peaks at about 11.64, 19.57, 21.99, 22.74 and 25.06 degrees 2θ were still present, indicating that crystal Form B had remained substantially unchanged. A similar lack of significant change in the XRPD pattern was also observed when a sample was stored at 40° C. for 25 minutes (see FIG. 6B).

Figure 7:
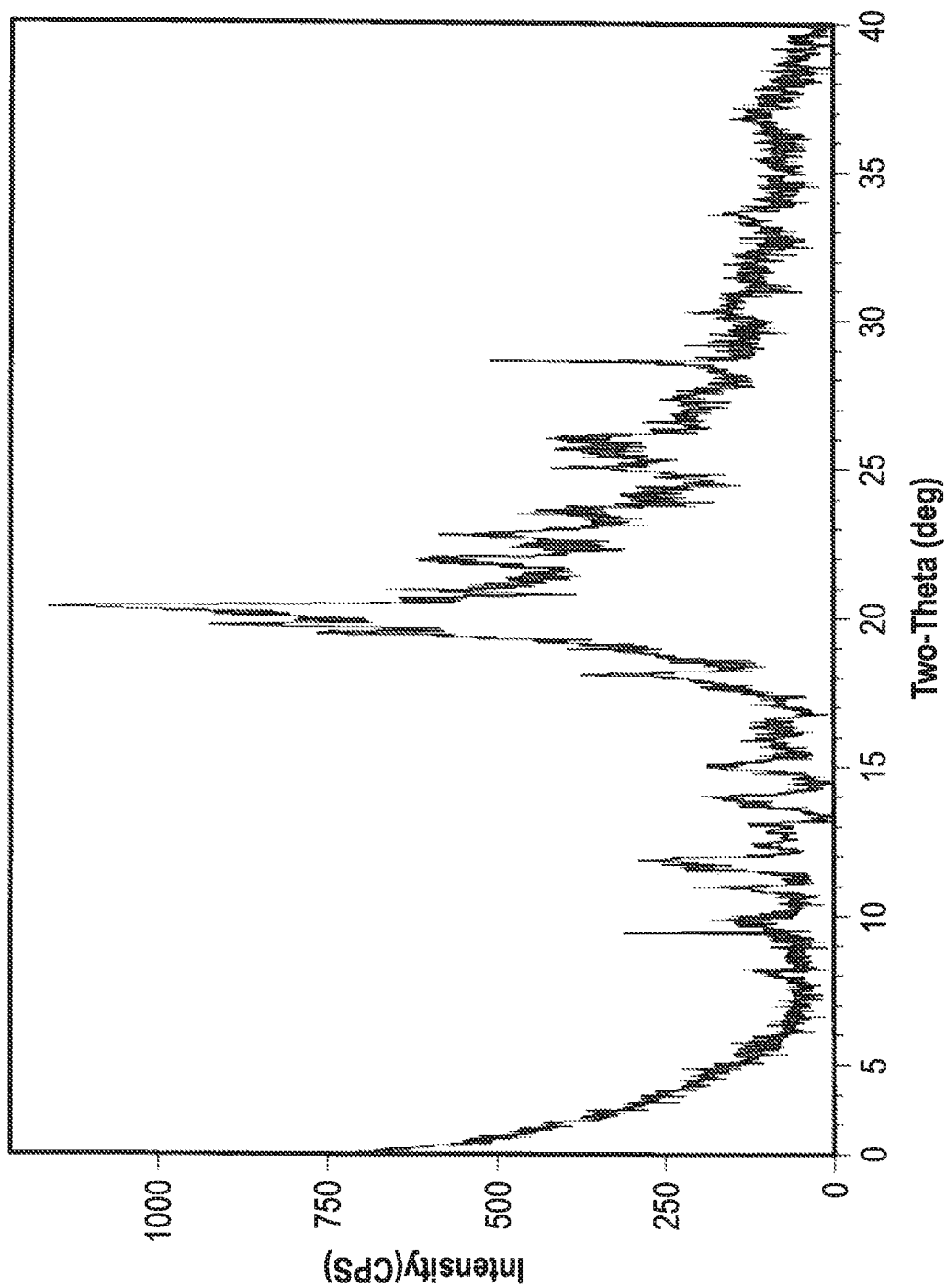
FIG. 7 presents an XRPD pattern of a sample of crystalline Form B after being maintained at 22±2° C. and relative humidity of 0% for 120 hours.

In addition, another sample of 10-50 grams of crystalline Form B was maintained at a temperature of 22±2° C. and relative humidity of 0% for 120 hours. When the XRPD spectrum of the sample after being maintained at 22±2° C. and relative humidity of 0% for 120 hours (see FIG. 7) was compared to the XRPD spectrum of the sample before being maintained under those conditions, the XRPD spectrum revealed the sample to be a poorly-crystalline mixture of Forms A and B.

Figure 8:
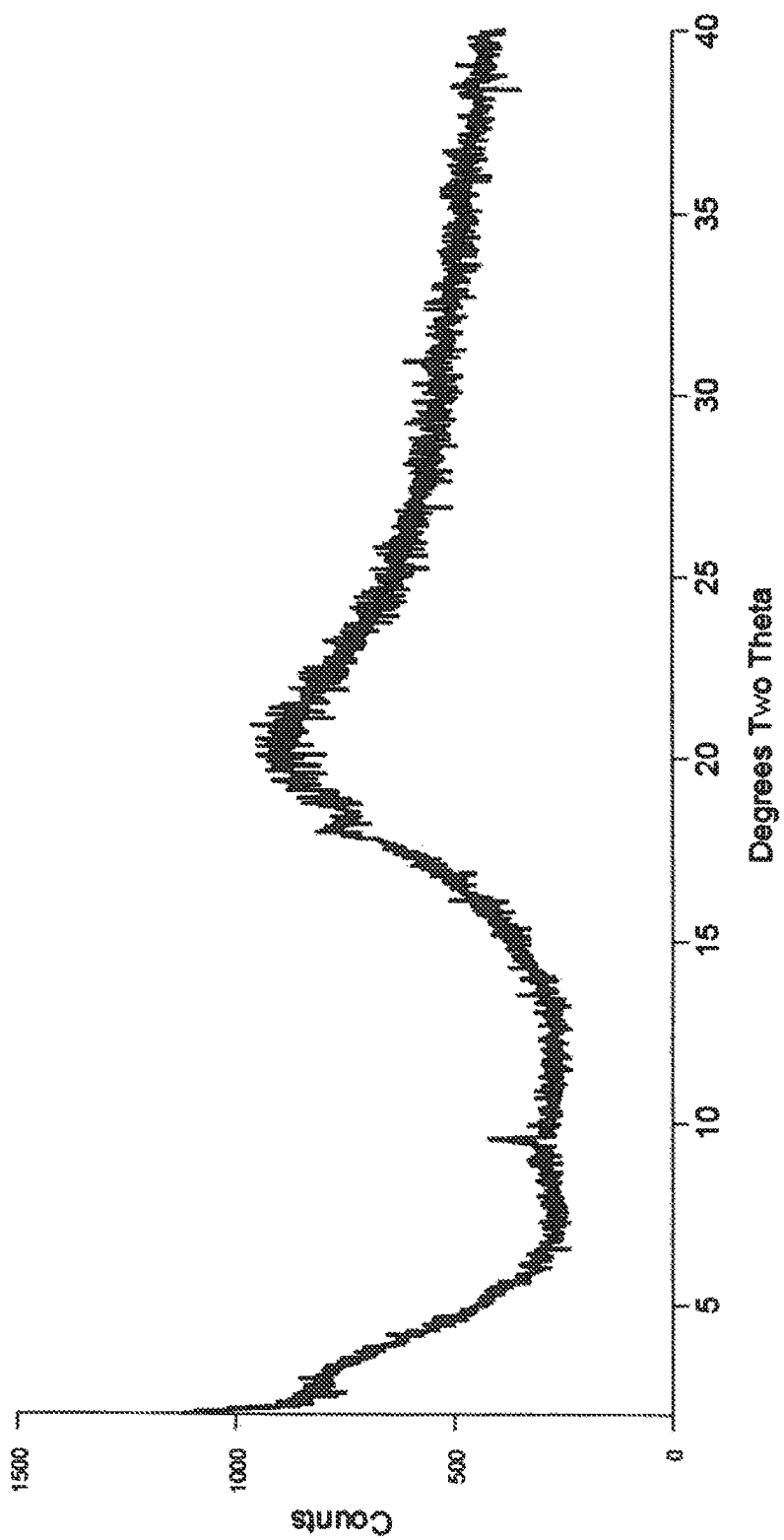
FIG. 8 presents an XRPD pattern of a sample of crystalline Form B after being maintained 40° C. for 16 hours.

In addition, a similar sample of crystalline Form B was maintained at a temperature of 40° C. for 16 hours. When the XRPD spectrum of the sample after being maintained 40° C. for 16 hours (see FIG. 8) was compared to the XRPD spectrum of the sample before being maintained under those conditions, the XRPD spectrum revealed the disappearance of peaks at about 11.64, 19.57, 21.99, 22.74 and 25.06 degrees 2θ, indicating that a substantial portion of crystalline Form B had converted to the amorphous form.

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

What is claimed is:

1. A crystalline form of 7-[3α,5α-dihydroxy-2-(3α-hydroxy-5-(3-(2,5-dichloro)thienyl)-1E-pentenyl)cyclopentyl]-5Z-heptenamide:

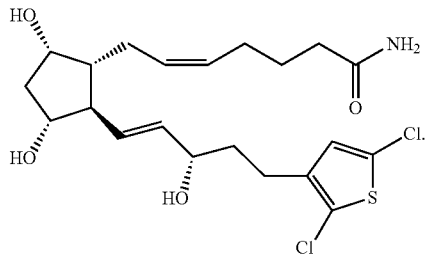 [SMILES: NC(=O)CCC/C=C\C[C@@H]1[C@@H](/C=C/[C@@H](O)CCc2cc(Cl)sc2Cl)[C@H](O)C[C@@H]1O]

having an X-ray powder diffraction pattern with peaks at 12.0±0.1, 14.1±0.1, 20.1±0.1, 20.5±0.1 and 23.7±0.1 degrees 2θ.

2. The crystalline form according to claim 1, wherein the crystalline form has the X-ray powder diffraction pattern substantially as shown in FIG. 1A.

3. The crystalline form according to claim 1, wherein the crystalline form is substantially free of other crystalline forms.

4. A crystalline form of 7-[3α,5α-dihydroxy-2-(3α-hydroxy-5-(3-(2,5-dichloro)thienyl)-1E-pentenyl)cyclopentyl]-5Z-heptenamide:

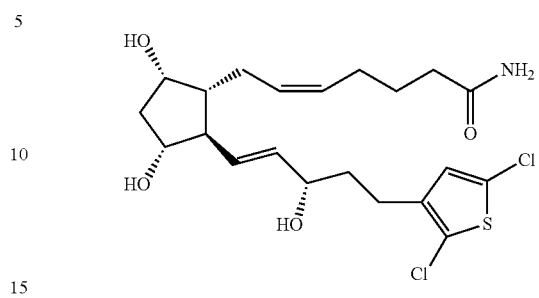

having an X-ray powder diffraction pattern with peaks at 11.6±0.1, 19.6±0.1, 22.0±0.1, 22.7±0.1 and 25.1±0.1 degrees 2θ.

5. The crystalline form according to claim 4, wherein the crystalline form has the X-ray powder diffraction pattern substantially as shown in FIG. 1B.

6. The crystalline form according to claim 4, wherein the crystalline form is substantially free of other crystalline forms.

* * * * *